(12) United States Patent
Stalewski et al.

(10) Patent No.: US 10,344,054 B2
(45) Date of Patent: Jul. 9, 2019

(54) ANGIOTENSIN-1-RECEPTOR ANTAGONISTS

(71) Applicant: Ferring B.V., Hoofddorp (NL)

(72) Inventors: Jacek Stalewski, San Diego, CA (US); Edward Earl Cable, San Diego, CA (US)

(73) Assignee: FERRING B.V., Hoofddorp (NL)

( * ) Notice: Subject to any disclaimer, the term of this patent is extended or adjusted under 35 U.S.C. 154(b) by 10 days.

(21) Appl. No.: 15/612,763

(22) Filed: Jun. 2, 2017

(65) Prior Publication Data

US 2017/0349629 A1 Dec. 7, 2017

Related U.S. Application Data

(60) Provisional application No. 62/344,831, filed on Jun. 2, 2016.

(30) Foreign Application Priority Data

Aug. 23, 2016 (EP) .................................... 16185403

(51) Int. Cl.
*A61K 38/00* (2006.01)
*C07K 7/06* (2006.01)
*C07K 7/14* (2006.01)

(52) U.S. Cl.
CPC .................. *C07K 7/06* (2013.01); *C07K 7/14* (2013.01); *A61K 38/00* (2013.01)

(58) Field of Classification Search
CPC ............. A61K 38/00; C07K 7/06; C07K 7/14
USPC ................. 514/1.1, 16.2, 16.3; 530/316, 300
See application file for complete search history.

(56) References Cited

U.S. PATENT DOCUMENTS 8,809,260 B2  8/2014 Yamashita et al.

FOREIGN PATENT DOCUMENTS

| WO | 2008/142576 A2 | 11/2008 |
| WO | 2010/077339 A2 | 7/2010 |

OTHER PUBLICATIONS

Bouley et al, "N- and C-terminal structure-activity study of angiotensin II nad the angiotensin AT2 recptor," European Journal of Pharmacology, 1998, 343: 323-331.*
Alwan, et al., Addendum: Sartan Treatment During Pregnancy, Clinical and Molecular Technology 73:904-905, 2005.
Bullo, et al., Pregnancy Outcome Following Exposure to Angiotensin-Converting Enzymes Inhibitors or Angiotensin Receptor Antagonists, downloaded from http://hyper.ahajournals.org on Feb. 9, 2016.
De Gasparo, et al., International Union of Pharmacology. XXIII. The Angiotensin II Receptors, Pharmacological Reviews 52:415-472, 2000.
Gavras, et al., The Angiotensin II Type I Receptor Blocker Losartan in Clinical Practice: a Review, Clinical Therapeutics vol. 18, No. 6, 1996 pp. 1058-1067.
Hata, et al., Effects of Two Angiotensin II Analogues on Blood Pressure, Plasma Aldosterone Concentration, Plasma Renin Activity and Creatinine Clearance in Normal Subjects on Different Sodium Intakes, Eur. J. Clin. Pharmacol. 18, 1980 pp. 295-299.
Hering, et al., Effects of Circulating and Local Uteroplacental Angiotensin II in Rat Pregnancy, downloaded from http://hyper.ahajournals.org on Mar. 26, 2014.
Nyeki, et al., Synthesis of Angiotensin II Antagonists with Variations in Position 5, Journal of Medicinal Chemistry, vol. 30, No. 10, 1987 pp. 1719-1724.
Samanen, et al., Effects of D-Amino Acid Substitution on Antagonist Activities of Angiotensin II Analogues, J. Med. Chem., vol. 31, 1988 pp. 510-516.
Violin, et al., Beta-arrestin-biased ligandsat the AT1R: a novel approach to the treatment of acute heart failure, Drug Discovery Today: Therapeutic Strategies vol. 9, No. 4, 2012 pp. 149-154.
Extended European Search Report dated Mar. 13, 2017 in corresponding application No. EP P16185403.9.

* cited by examiner

*Primary Examiner* — Julie Ha
(74) *Attorney, Agent, or Firm* — Foley & Lardner LLP

(57) ABSTRACT

Compounds of formula (I) and pharmaceutically acceptable salts thereof are described:

AA1-Arg-Val-AA4-AA5-His-Pro-AA8-OH    (I), in which AA1, AA4, AA5, and AA8 are defined in the specification. The compounds of formula (I) can be used to treat hypertension (e.g., hypertension induced by pregnancy), preeclampsia, or a renal disease induced by pregnancy.

28 Claims, No Drawings

ANGIOTENSIN-1-RECEPTOR ANTAGONISTS

CROSS-REFERENCE TO RELATED APPLICATIONS

The present application claims priority to European Patent Application Serial No. 16185403.9, filed on Aug. 23, 2016, and U.S. Provisional Application Ser. No. 62/344,831, filed on Jun. 2, 2016. The contents of the prior applications are hereby incorporated by reference in its entirety.

TECHNICAL FIELD

This invention relates to certain angiotensin-1-receptor antagonists, as well as related compositions and methods.

BACKGROUND

The renin-angiotensin system (RAS) or renin-angiotensin-aldosterone system (RAAS) is a hormonal system that regulates blood pressure and fluid balance. Blocking the RAS can reduce blood pressure. As such, clinical interventions blocking RAS, including inhibitors of angiotensin-converting enzyme (ACE) and angiotensin receptor blockers (ARBs), have been developed to treat hypertension.

Typically, the prohormone angiotensinogen is converted to the inactive precursor Angiotensin I, which is then converted by ACE to the active peptide hormone Angiotensin II (Ang II). Ang II can be further metabolized to Ang III, Ang IV, and Ang(1-7).

In humans, Ang II effects are mediated through seven-transmembrane G-protein coupled receptors, including angiotensin-1-receptor (AT1R) and angiotensin-2-receptor (AT2R). The blood pressure effects of Ang II are primarily mediated by AT1R. Activation of the AT1R can lead to various effects, including vasoconstriction leading to increased blood pressure. Conversely, blocking the AT1R can reduce blood pressure. Several angiotensin receptor blockers have been developed to treat hypertension.

One of the first angiotensin receptor blockers (ARBs) developed was the peptidic AT1R antagonist saralasin (i.e., [Sar1, Val5, Ala8]AngII) in the 1970's, which was approved by the FDA and sold as SARENIN in the US. Another peptidic antagonist, sarilesin (i.e., [Sar1, Ile8]AngII) entered clinical trials in Japan.

Clinical utility of both these compounds was limited by several factors, including partial agonist activity, short duration of action, and administration by continuous intravenous infusion. Subsequently, research and development activities in this area turned to the sartan class of non-peptidic small molecule ARBs, such as losartan, valsartan, and others, which did not have partial agonist activity and could be given orally. Several non-peptidic ARBs have been approved for therapeutic use, and SARENIN was withdrawn from the market.

The sartan class of non-peptidic small molecule ARBs are not recommended for use during pregnancy. Fetal exposure to ARBs can lead to neonatal and long-term complications. For example, it has been recommended that maternal treatment with the sartans be avoided in second and third trimesters of pregnancy. Thus, there is a lack of treatment options for hypertension disorders during pregnancy.

SUMMARY

This disclosure is based on the unexpected discovery that certain peptide compounds exhibited angiotensin-1-receptor antagonist activities with no or reduced agonist activities. These compounds can also have reduced fetal exposure and can be effective in treating hypertension disorders (e.g., chronic hypertension or gestational hypertension) or preeclampsia during pregnancy without causing fetal or neonatal complications.

In one aspect, this disclosure features compounds of formula (I) or pharmaceutically acceptable salts thereof:

AA1-Arg-Val-AA4-AA5-His-Pro-AA8-OH    (I), in which AA1 is an amino acid residue selected from the group consisting of sarcosine and ((2S,3R,4R,5R)-2,3,4,5,6-pentahydroxyhexyl)glycine; AA4 is an amino acid residue selected from the group consisting of tyrosine or meta-tyrosine, each of which is optionally substituted with at least one substituent selected from the group consisting of halo and hydroxyl; AA5 is an amino acid residue selected from the group consisting of valine, leucine, isoleucine, glycine, alanine, phenylalanine, threonine, lysine, and tyrosine, each of which is optionally substituted with at least one substituent selected from the group consisting of $C_{1-6}$ alkyl, $C_{4-6}$ cycloalkyl, $NH_2$, aryl, and heteroaryl; and AA8 is an amino acid residue selected from the group consisting of 1-naphthylalanine, (3-benzothienyl)alanine, and phenylalanine substituted with at least one substituent selected from the group consisting of $C_{1-6}$ alkyl, $C_{1-6}$ haloalkyl, $C_{4-6}$ cycloalkyl, halo, CN, aryl, and heteroaryl, in which the at least one substituent is at the 2-position on the phenyl ring of the phenylalanine. AA8 is a D-amino acid residue, and each of Arg, Val, AA4, AA5, His, and Pro in formula (I) is an L-amino acid residue.

In another aspect, this disclosure features a pharmaceutical composition comprising at least one of the compounds of formula (I) or a pharmaceutically acceptable salt thereof and a pharmaceutically acceptable carrier.

In another aspect, this disclosure features a method of treating hypertension (e.g., hypertension induced by pregnancy). The method includes administering to a patient in need thereof an effective amount of the pharmaceutical composition described herein.

In still another aspect, this disclosure features a method of treating preeclampsia or a renal disease induced by pregnancy. The method includes administering to a patient in need thereof an effective amount of the pharmaceutical composition described herein.

In a further aspect, there is provided a composition (e.g. a pharmaceutical composition) for use in the treatment of hypertension (e.g., hypertension induced by pregnancy), preeclampsia or a renal disease (e.g. renal disease induced by pregnancy), the composition comprising a compound of formula (I) or a pharmaceutically acceptable salt thereof and a pharmaceutically acceptable carrier.

In a further aspect, there is provided the use of a compound of formula (I) or a pharmaceutically acceptable salt thereof in the manufacture of a medicament for the treatment of hypertension (e.g., hypertension induced by pregnancy), preeclampsia or a renal disease (e.g. renal disease induced by pregnancy).

Other features, objects, and advantages will be apparent from the description, drawings, and the claims.

DETAILED DESCRIPTION

This disclosure generally relates to AT1R antagonists (e.g., AT1R antagonist peptides) and their use for treating hypertension, preeclampsia, or a renal disease (e.g., in patients during pregnancy).

In some embodiments, the AT1R antagonist peptides described herein are compounds of formula (I) or a pharmaceutically acceptable salt thereof:

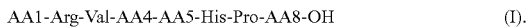

AA1-Arg-Val-AA4-AA5-His-Pro-AA8-OH (I).

In formula (I), AA1 is an amino acid residue selected from the group consisting of sarcosine and ((2S,3R,4R,5R)-2,3,4,5,6-pentahydroxyhexyl)glycine; AA4 is an amino acid residue selected from the group consisting of tyrosine or meta-tyrosine, each of which is optionally substituted with at least one substituent selected from the group consisting of halo and hydroxyl; AA5 is an amino acid residue selected from the group consisting of valine, leucine, isoleucine, glycine, alanine, phenylalanine, threonine, lysine, and tyrosine, each of which is optionally substituted with at least one substituent selected from the group consisting of $C_{1-6}$ alkyl, $C_{4-6}$ cycloalkyl, $NH_2$, aryl, and heteroaryl; and AA8 is an amino acid residue selected from the group consisting of alanine substituted with at least one substituent selected from the group consisting of 1-naphthylalanine, (3-benzothienyl)alanine, and phenylalanine substituted with at least one substituent selected from the group consisting of $C_{1-6}$ alkyl, $C_{1-6}$ haloalkyl, $C_{4-6}$ cycloalkyl, halo, CN, aryl (e.g., phenyl, 1-naphthyl, or 2-naphthyl), and heteroaryl, in which the at least one substituent is at the 2-position on the phenyl ring of the phenylalanine. AA8 is a D-amino acid residue and each of Arg, Val, AA4, AA5, His, and Pro in formula (I) is an L-amino acid residue.

The term "alkyl" refers to a saturated, linear or branched hydrocarbon moiety, such as —$CH_3$ or —$CH(CH_3)_2$. The term "haloalkyl" refers to a saturated, linear or branched hydrocarbon moiety substituted by at least one halo group (e.g., F, Cl, Br, or I), such as —$CH_2Cl$ or —$CF_3$. The term "cycloalkyl" refers to a saturated, cyclic hydrocarbon moiety, such as cyclobutyl, cyclopentyl, or cyclohexyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridinyl, pyrimidinyl, quinazolinyl, quinolyl, isoquinolyl, benzothienyl, and indolyl.

In some embodiments, AA4 can be tyrosine optionally substituted with at least one substituent, in which the at least one substituent is at the 3-position on the phenyl ring of the tyrosine. For example, AA4 can be tyrosine, meta-tyrosine, 3-hydroxytyrosine, or 3-chlorotyrosine.

In some embodiments, AA5 can be an amino acid residue selected from the group consisting of valine, leucine, isoleucine, glycine, alanine, phenylalanine, threonine, lysine, and tyrosine, each of which is optionally substituted with at least one substituent selected from the group consisting of $CH_3$, cyclobutyl, cyclopentyl, cyclohexyl, $NH_2$, thienyl, and thiazolyl. For example, AA5 can be valine, isoleucine, cyclobutylglycine, cyclopentylglycine, cyclohexylglycine, cyclohexylalanine, leucine, o-methyl threonine, lysine, phenylalanine, tyrosine, 4-aminophenylalanine, 3-thienylalanine, 2-thienylalanine, or 4-thiazolylalanine.

In some embodiments, AA8 can be an amino acid residue selected from the group consisting of unsubstituted D-1-naphthylalanine, unsubstituted D-(3-benzothienyl)alanine, and D-phenylalanine substituted with at least one substituent selected from the group consisting of $CH_3$, $CF_3$, Cl, Br, CN, and phenyl. For example, AA8 can be D-1-naphthylalanine, D-(3-benzothienyl)alanine, D-2-chlorophenylalanine, D-2-bromophenylalanine, D-2-methylphenylalanine, D-2-trifluoromethylphenylalanine, D-2-cyanophenylalanine, D-2-phenylphenylalanine, D-2,4-dichlorophenylalanine, or D-2,6-dimethylphenylalanine. Without wishing to be bound by theory, it is believed that the amino acid residues of AA8 described above can help reduce or eliminate the angiotensin-1-receptor agonist activities in the compounds of formula (I).

In some embodiments, when AA5 or AA8 is an amino acid substitute with a heteroaryl group, the heteroaryl group can include one, two, or three aromatic rings, each of which can be a five-membered or six-membered ring. In such embodiments, the heteroaryl group can include one, two, three, or more ring heteroatoms, such as N, O, or S. For example, the heteroaryl group can be a group that includes one aromatic ring containing one ring heteroatom (e.g., N, O, or S), one aromatic ring containing two ring heteroatoms (e.g., N, O, or S), one aromatic ring containing three ring heteroatoms (e.g., N, O, or S), two aromatic rings containing one ring heteroatom (e.g., N, O, or S), two aromatic rings containing two ring heteroatoms (e.g., N, O, or S), or two aromatic rings containing three ring heteroatoms (e.g., N, O, or S).

In some embodiments, AA1 can be sarcosine. In such embodiments, AA4 can be tyrosine, meta-tyrosine, 3-hydroxytyrosine, or 3-chlorotyrosine; AA5 can be valine, isoleucine, lysine, tyrosine, 4-aminophenylalanine, cyclohexylalanine, cyclopentylglycine, cyclohexylglycine, phenylalanine, o-methyl threonine, 3-thienylalanine, 2-thienylalanine, or 4-thiazolylalanine; and AA8 can be D-1-naphthylalanine, D-(3-benzothienyl)alanine, D-2-chlorophenylalanine, D-2-bromophenylalanine, D-2-methylphenylalanine, D-2-trifluoromethylphenylalanine, D-2-cyanophenylalanine, D-2-phenylphenylalanine, D-2,4-dichlorophenylalanine, or D-2,6-dimethylphenylalanine.

In some embodiments, AA1 can be ((2S,3R,4R,5R)-2,3,4,5,6-pentahydroxyhexyl)glycine. In such embodiments, AA4 can be tyrosine; AA5 can be valine or cyclohexylglycine; and AA8 can be D-1-naphthylalanine, D-(3-benzothienyl)alanine, D-2-chlorophenylalanine, D-2-methylphenylalanine, or D-2-phenylphenylalanine.

Exemplary compounds of formula (I) (i.e., Compounds 1-46) include those listed in Table 1 below. Table 1 also includes reference compounds 1-4. Unless specified otherwise, the amino acid code in Table 1 refers to its L-isomer except for Sar (which is achiral) and Glac (whose chirality is not on the alpha carbon atom).

TABLE 1

| Cpd # | Compound Names in Abbreviation |
|---|---|
| 1 | Sar-Arg-Val-Tyr-Val-His-Pro-(D-1Nal)-OH |
| 2 | Sar-Arg-Val-Tyr-Lys-His-Pro-(D-1Nal)-OH |
| 3 | Sar-Arg-Val-Tyr-Val-His-Pro-(D-Phe(2-CF₃))—OH |
| 4 | Sar-Arg-Val-Tyr-Val-His-Pro-(D-Phe(2-Cl))—OH |
| 5 | Sar-Arg-Val-Tyr-Val-His-Pro-(D-Phe(2-CN))—OH |
| 6 | Sar-Arg-Val-Tyr-Val-His-Pro-(D-Phe(2-Ph))—OH |
| 7 | Sar-Arg-Val-Tyr-Val-His-Pro-(D-Phe(2,4-diCl))—OH |
| 8 | Sar-Arg-Val-Tyr-Val-His-Pro-(D-Phe(2,6-diMe))—OH |
| 9 | Sar-Arg-Val-Tyr-Val-His-Pro-(D-Phe(2-Me))—OH |
| 10 | Sar-Arg-Val-Tyr-Val-His-Pro-(D-(3-benzothienyl)alanine)-OH |
| 11 | Sar-Arg-Val-Tyr-Val-His-Pro-(D-Phe(2-Br))—OH |
| 12 | Sar-Arg-Val-Tyr-Tyr-His-Pro-(D-1Nal)-OH |
| 13 | Sar-Arg-Val-Tyr-Aph-His-Pro-(D-1Nal)-OH |
| 14 | Sar-Arg-Val-Tyr-Cha-His-Pro-(D-1Nal)-OH |
| 15 | Sar-Arg-Val-Tyr-Cpg-His-Pro-(D-1Nal)-OH |
| 16 | Sar-Arg-Val-Tyr-Phe-His-Pro-(D-1Nal)-OH |
| 17 | Sar-Arg-Val-Tyr-Thr(Me)-His-Pro-(D-1Nal)-OH |

TABLE 1-continued

| Cpd # | Compound Names in Abbreviation |
|---|---|
| 18 | Sar-Arg-Val-Tyr-Cpg-His-Pro-(D-Phe(2-Cl))—OH |
| 19 | Sar-Arg-Val-Tyr-Chg-His-Pro-(D-Phe(2-Cl))—OH |
| 20 | Sar-Arg-Val-Tyr-Aph-His-Pro-(D-Phe(2-Cl))—OH |
| 21 | Sar-Arg-Val-Tyr-Thr(Me)-His-Pro-(D-Phe(2-Cl))—OH |
| 22 | Sar-Arg-Val-Tyr-(3-Thi)-His-Pro-(D-Phe(2-Cl))—OH |
| 23 | Sar-Arg-Val-Tyr-(2-Thi)-His-Pro-(D-Phe(2-Cl))—OH |
| 24 | Sar-Arg-Val-Tyr-(Ala(4-Thz))-His-Pro-(D-Phe(2-Cl))—OH |
| 25 | Sar-Arg-Val-Tyr-Ile-His-Pro-(D-Phe(2-Cl))—OH |
| 26 | Sar-Arg-Val-Tyr-Chg-His-Pro-(D-Phe(2-CF₃))—OH |
| 27 | Sar-Arg-Val-Tyr-Chg-His-Pro-(D-Phe(2-Me))—OH |
| 28 | Sar-Arg-Val-Tyr(3-Cl)-Val-His-Pro-(D-Phe(2-Cl))—OH |
| 29 | Glac-Arg-Val-Tyr-Val-His-Pro-(D-Phe(2-Cl))—OH |
| 30 | Sar-Arg-Val-(m-Tyr)-Val-His-Pro-(D-Phe(2-Cl))—OH |
| 31 | Glac-Arg-Val-Tyr-Chg-His-Pro-(D-Phe(2-Cl))—OH |
| 32 | Sar-Arg-Val-DOPA-Val-His-Pro-(D-Phe(2-Cl))—OH |
| 33 | Sar-Arg-Val-Aph-Val-His-Pro-(D-Phe(2-Cl))—OH |
| 34 | Sar-Arg-Val-Tyr-Chg-His-Pro-(D-1Nal)-OH |
| 35 | Sar-Arg-Val-Tyr-Chg-His-Pro-(D-(3-benzothienyl) alanine)-OH |
| 36 | Sar-Arg-Val-Tyr-Chg-His-Pro-(D-Phe(2-Ph))—OH |
| 37 | Glac-Arg-Val-Tyr-Val-His-Pro-(D-1Nal)-OH |
| 38 | Glac-Arg-Val-Tyr-Val-His-Pro-(D-(3-benzothienyl) alanine)-OH |
| 39 | Glac-Arg-Val-Tyr-Val-His-Pro-(D-Phe(2-Ph))—OH |
| 40 | Glac-Arg-Val-Tyr-Chg-His-Pro-(D-1Nal)-OH |
| 41 | Glac-Arg-Val-Tyr-Chg-His-Pro-(D-(3-benzothienyl) alanine)-OH |
| 42 | Glac-Arg-Val-Tyr-Chg-His-Pro-(D-Phe(2-Ph))—OH |
| 43 | Glac-Arg-Val-Tyr-Cpg-His-Pro-(D-Phe(2-Cl))—OH |
| 44 | Glac-Arg-Val-Tyr-Cpg-His-Pro-(D-Phe(2-Me))—OH |
| 45 | Glac-Arg-Val-Tyr-Val-His-Pro-(D-Phe(2-Me))—OH |
| 46 | Glac-Arg-Val-Tyr-Chg-His-Pro-(D-Phe(2-Me))—OH |
| Reference compound 1 | Sar-Arg-Val-Tyr-Ile-His-Pro-Ile-OH |
| Reference compound 2 | Sar-Arg-Val-Tyr-Ile-His-Pro-D-Phe-OH |
| Reference compound 3 | Asp-Arg-Val-Tyr-Ile-His-Pro-Phe-OH |
| Reference compound 4 | Valsartan |

The full names of the abbreviations of the native or non-native amino acids used in this disclosure are summarized in Table 2 below:

TABLE 2

| Abbreviation | Full name |
|---|---|
| Glac | ((2S,3R,4R,5R)-2,3,4,5,6-pentahydroxyhexyl) glycine |
| Sar | Sarcosine |
| Arg | Arginine |
| Val | Valine |
| Ile | Isoleucine |
| His | Histidine |
| Pro | Proline |
| Cbg | Cyclobutylglycine |
| Cpg | Cyclopentylglycine |
| Chg | Cyclohexylglycine |
| Cha | Cyclohexylalanine |
| Leu | Leucine |
| Thr(Me) | O-Methyl threonine |
| Lys | Lysine |
| Phe | Phenylalanine |
| D-Phe(2-CF₃) | 2-Trifluoromethylphenylalanine |
| D-Phe(2-Cl) | 2-Chlorophenylalanine |
| D-Phe(2-CN) | 2-Cyanophenylalanine |
| D-Phe(2-Ph) | 2-Phenylphenylalanine |
| D-Phe(2-Me) | 2-Methylphenylalanine |
| D-Phe(2-Br) | 2-Bromophenylalanine |
| D-Phe(2,4-diCl) | 2,4-Dichlorophenylalanine |
| D-Phe(2,6-diMe) | 2,6-Dimethylphenylalanine |
| Tyr | Tyrosine |
| m-Tyr | meta-Tyrosine |
| DOPA | 3-Hydroxytyrosine |

TABLE 2-continued

| Abbreviation | Full name |
|---|---|
| Tyr(3-Cl) | 3-Chlorotyrosine |
| D-1Nal | D-1-Naphthylalanine |
| Aph | 4-Aminophenylalanine |
| 3-Thi | 3-Thienylalanine |
| 2-Thi | 2-Thienylalanine |
| Ala(4-Thz) | 4-Thiazolylalanine |

In some embodiments, the compound of formula (I) may be (4) Sar-Arg-Val-Tyr-Val-His-Pro-(D-Phe(2-Cl))—OH
(9) Sar-Arg-Val-Tyr-Val-His-Pro-(D-Phe(2-Me))—OH;
(29) Glac-Arg-Val-Tyr-Val-His-Pro-(D-Phe(2-Cl))—OH;
(31) Glac-Arg-Val-Tyr-Chg-His-Pro-(D-Phe(2-Cl))—OH;
(45) Glac-Arg-Val-Tyr-Val-His-Pro-(D-Phe(2-Me))—OH; or
(46) Glac-Arg-Val-Tyr-Chg-His-Pro-(D-Phe(2-Me))—OH.

The AT1R antagonist peptides described herein (e.g., the compounds of formula (I)) can be made by methods known in the art or methods described herein. Examples 1-6 below provide detailed descriptions of how compounds 1-46 were actually prepared.

The reactions for preparing the AT1R antagonist peptides described herein can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the AT1R antagonist peptides described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

The AT1R antagonist peptides described herein can also include all isotopes of atoms occurring in the intermediates or final compounds. Isotopes include those atoms having the same atomic number but different mass numbers. For example, isotopes of hydrogen include tritium and deuterium.

All compounds and pharmaceutically acceptable salts thereof, can be found together with other substances such as water and solvents (e.g. hydrates and solvates) or can be isolated.

In some embodiments, the AT1R antagonist peptides described herein are substantially isolated. By "substantially isolated" is meant that a compound is at least partially or substantially separated from the environment in which it was formed or detected. Partial separation can include, for example, a composition enriched with an AT1R antagonist peptide described herein. Substantial separation can include compositions containing at least about 50%, at least about 60%, at least about 70%, at least about 80%, at least about 90%, at least about 95%, at least about 97%, or at least about 99% by weight of an AT1R antagonist peptide described herein. Methods for isolating compounds and their salts are routine in the art.

This disclosure also features pharmaceutical compositions containing a therapeutically effective amount of at least one (e.g., two or more) of the AT1R antagonist peptides described herein (e.g., the compounds of formula (I)) or a pharmaceutically acceptable salt thereof as an active ingredient, as well as at least one pharmaceutically acceptable carrier (e.g., adjuvant or diluent). Examples of pharmaceutically acceptable salts include acid addition salts, e.g., salts formed by reaction with hydrohalogen acids (such as hydrochloric acid or hydrobromic acid), mineral acids (such as sulfuric acid, phosphoric acid and nitric acid), and aliphatic, alicyclic, aromatic or heterocyclic sulfonic or carboxylic acids (such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid, and naphthalenesulphonic acid).

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical carriers for delivery of an active AT1R antagonist peptide. Examples of other carriers include colloidal silicon oxide, magnesium stearate, cellulose, sodium lauryl sulfate, and D&C Yellow #10.

The pharmaceutical composition described herein can optionally include at least one further additive selected from a disintegrating agent, binder, lubricant, flavoring agent, preservative, colorant and any mixture thereof. Examples of such and other additives can be found in "Handbook of Pharmaceutical Excipients"; Ed. A. H. Kibbe, 3rd Ed., American Pharmaceutical Association, USA and Pharmaceutical Press UK, 2000.

The pharmaceutical composition described herein can be adapted for parenteral, oral, topical, nasal, rectal, buccal, or sublingual administration or for administration via the respiratory tract, e.g., in the form of an aerosol or an air-suspended fine powder. The term "parenteral" as used herein refers to subcutaneous, intracutaneous, intravenous, intramuscular, intraarticular, intraarterial, intrasynovial, intrasternal, intrathecal, intralesional, intraperitoneal, intraocular, intra-aural, or intracranial injection, as well as any suitable infusion technique. In some embodiments, the composition can be in the form of tablets, capsules, powders, microparticles, granules, syrups, suspensions, solutions, nasal spray, transdermal patches or suppositories.

In some embodiments, the pharmaceutical composition described herein can contain an AT1R antagonist peptide described herein that is dissolved in an aqueous solution. For example, the composition can include a sodium chloride aqueous solution (e.g., containing 0.9 wt % of sodium chloride) to serve as a diluent.

In addition, this disclosure features a method of using an AT1R antagonist peptide as outlined above for treating hypertension or preeclampsia, or for the manufacture of a medicament for such a treatment. The method can include administering to a patient (e.g., a patient during pregnancy) in need thereof an effective amount of the pharmaceutical composition described herein. In some embodiments, the hypertension is induced by pregnancy. In some embodiments, the hypertension can be chronic hypertension or gestational hypertension. "An effective amount" refers to the amount of the pharmaceutical composition that is required to confer a therapeutic effect on the treated subject. Effective doses will vary, as recognized by those skilled in the art, depending on the types of diseases treated, route of administration, excipient usage, and the possibility of co-usage with other therapeutic treatment.

As used herein, the terms "treatment," "treat," and "treating" refer to reversing, alleviating, delaying the onset of, or inhibiting the progress of, a disease or disorder described herein or one or more symptoms thereof. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The typical dosage of the AT1R antagonist peptide described herein can vary within a wide range and will depend on various factors such as the individual needs of each patient and the route of administration. Exemplary daily dosages (e.g., for subcutaneous administration) can be at least about 0.5 mg (e.g., at least about 1 mg, at least about 5 mg, at least about 10 mg, or at least about 15 mg) and/or at most about 200 mg (e.g., at most about 150 mg, at most about 100 mg, at most about 75 mg, at most about 50 mg, at most about 20 mg, or at most about 15 mg) of an AT1R antagonist peptide. The skilled person or physician may consider relevant variations to this dosage range and practical implementations to accommodate the situation at hand.

In some embodiments, the pharmaceutical composition described herein can be administered once daily. In some embodiments, the pharmaceutical composition can be administered more frequent than once daily (e.g., twice daily, three times daily, or four times daily). In some embodiments, the pharmaceutical composition can be administered by a continuous infusion, such as intravenous (IV) or subcutaneous (SC) infusion. In some embodiments, the pharmaceutical composition can be administered less frequent than once daily (e.g., once every two days, once every three days, or once every week).

In addition, this disclosure features a composition as outlined above, for use in treating hypertension or preeclampsia.

In some embodiments, the hypertension is induced by pregnancy. In some embodiments, the hypertension can be chronic hypertension or gestational hypertension.

The contents of all publications cited herein (e.g., patents, patent application publications, and articles) are hereby incorporated by reference in their entirety.

The following examples are illustrative and not intended to be limiting.

EXAMPLE

General Synthetic Methods
1. Amino Acid Derivatives

Amino acid derivatives were purchased from commercial providers (such as Aapptec, Chem Impex International, EMD Millipore, PPL, PepTech and Peptides International), except for Fmoc-D-Phe(2-Phe) and Fmoc-Thr(Me). Fmoc-D-Phe(2-Phe) and Fmoc-Thr(Me) were prepared as follows:

Synthesis of Fmoc-D-Phe(2-Ph)

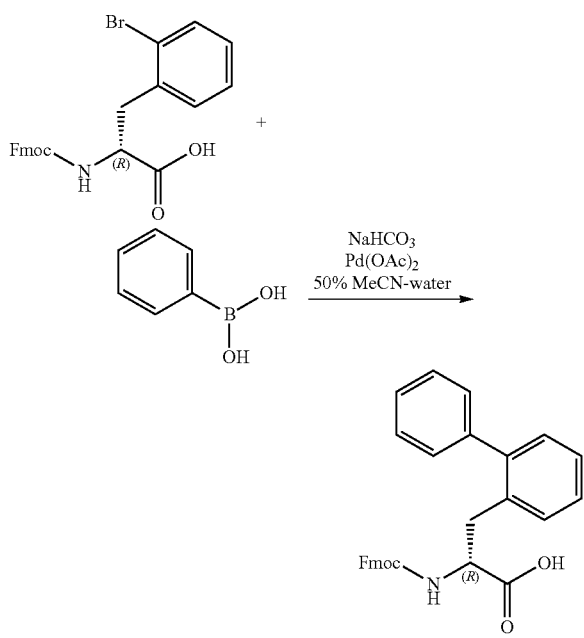

Fmoc-D-Phe(2-Br)-OH (923 mg, 2 mmol), phenylboronic acid (366 mg, 3 mmol), palladium(II) acetate (22 mg, 0.1 mmol), sodium bicarbonate (504 mg, 6 mmol) and 50% acetonitrile-water (10 ml) were combined inside a microwave-compatible glass vial. Argon was bubbled through the mixture for 1 minute and the vial was immediately crimped. The reaction mixture was heated at 70° C. with stirring for 30 minutes inside a microwave reactor (Biotage). Elemental palladium formed during the reaction was filtered off on celite. The filtrate was placed in a 50 ml centrifuge tube, was acidified with HCl, and was diluted with water to capacity. The oily product was separated by centrifugation. The pellet was washed with water, dissolved in tert-butanol and lyophilized to give the target product as a white powder. Yield: 930 mg (100%).

Synthesis of Fmoc-Thr(Me)

O-Methyl threonine (2.663 g, 20 mmol) was dissolved in a solution of sodium bicarbonate (5.04 g, 60 mmol) in water (100 ml). Acetonitrile (50 ml) was added, followed by a suspension of Fmoc-OSu (6.747 g, 20 mmol) in acetonitrile (50 ml), delivered in several portions. The reaction mixture was stirred for 2 hours and, during which time, became homogenous. It was then acidified with 2 M HCl and was diluted with 100 ml of water. The resulting precipitate was collected by filtration, washed with water and dried under vacuum to give the target product as a white powder. Yield: 6.745 g (95%).

2. Peptide Synthesis

Resins were purchased from Peptides International. D-Glucamine was purchased from ChemImpex or from TCI America. All additional reagents, chemicals and solvents were purchased from Sigma-Aldrich and VWR.

The compounds described herein were synthesized by standard methods in solid phase peptide chemistry utilizing Fmoc methodology. The peptides were assembled either manually or automatically using a Tribute peptide synthesizer or Symphony peptide synthesizer (Protein Technologies Inc., Tucson, Ariz.), or by combination of manual and automatic syntheses.

Preparative HPLC was performed on a Waters Prep LC System a Waters Sunfire C18 column, 100 Å, 5 μm, 30×100 mm at a flow rate of 40 mL/min or on a 50×100 mm column at a flow rate of 80 mL/min. Analytical reverse phase HPLC was performed on an Agilent Technologies 1200rr Series liquid chromatograph using an Agilent Zorbax C18 column, 1.8 μm, 2.6×50 mm at a flow rate of 0.6 mL/min or Agilent Zorbax C18 column, 1.8 μm, 4.6×50 mm at a flow rate of 2 mL/min. Final compound analyses were performed on an Agilent Technologies 1200 Series chromatograph by reverse phase HPLC on a Phenomenex Gemini 110 Å C18 column, 3 μm, 2×150 mm at a flow rate of 0.3 mL/min. Mass spectra were recorded on a MAT Finnigan LCQ electrospray mass spectrometer or on LTQ XL electrospray mass spectrometer (Thermo Scientific). Unless stated otherwise, all reactions were performed at room temperature. The following standard reference literature provides further guidance on general experimental set up, as well as on the availability of required starting material and reagents: Kates, S. A., Albericio, F., Eds., Solid Phase Synthesis: A Practical Guide, Marcel Dekker, New York, Basel, 2000; Greene, T. W., Wuts, P. G. M., Protective Groups in Organic Synthesis, John Wiley Sons Inc., $2^{nd}$ Edition, 1991; Stewart, J. M., Young, J. D., Solid Phase Synthesis, Pierce Chemical Company, 1984; Bisello, et al., J. Biol. Chem. 1998, 273, 22498-22505; Merrifield, J. Am. Chem. Soc. 1963, 85, 2149-2154; and Chang and White P. D., 'Fmoc Solid Phase Peptide Synthesis: a Practical Approach', Oxford University Press, Oxford, 2000.

The following protecting groups were utilized to protect the given amino acid side chain functional groups: Pbf (2,2,4,6,7-pentamethyldihydrobenzofuran-5-sulfonyl) for Arg; tBu (t-butyl) for Tyr; Boc (t-butoxycarbonyl) for Lys; and Trt (trityl) for His.

Each synthesis started with manual attachment of the first amino acid to 2-chlorotrityl resin. Generally, Fmoc-amino acid was dissolved in dichloromethane (DCM) at the concentration of 0.1-0.2 M, followed by addition of N,N-diisopropylethylamine (DIPEA) (5 eq). The resulting solution was added to dry 2-chlorotrityl resin (2 eq). The mixture was reacted for 4 hours, followed by addition of methanol (10% v/v). After another 30 minutes, the reagents were drained and the resin was washed with DMF.

Couplings of Fmoc-protected amino acids on the Tribute synthesizer were mediated with HBTU/NMIVI in DMF. Single cycles of 60 minutes with a 3-5-fold excess of activated Fmoc-protected amino acids were used during the synthesis. Arginine was coupled over 3 hours. Removal of the Fmoc protecting group was monitored by UV. Multiple (up to 10 times, as needed) two-minute washes of the peptide resin with 20% piperidine in DMF were performed.

Couplings of Fmoc-protected amino acids on the Symphony synthesizer were mediated with HBTU/DIPEA in NMP. Single cycles of 60 minutes with a 3-5-fold excess of activated Fmoc-protected amino acids were used during the synthesis. Arginine was coupled over 3 hours. Removal of the Fmoc protecting group was accomplished with two washes of the peptide resin with 20% piperidine in DMF (5 minutes wash followed by 20 minutes wash).

DIC/HOBt or DIC/Oxyma Pure mediated couplings in DMF were employed for all amino acids in manual mode. Single cycles of at least 2 hours with up to 3-fold excess of activated Fmoc-protected amino acids were used during the synthesis. The completeness of couplings was assessed with ninhydrin (Kaiser) test. Removal of the Fmoc protecting group was achieved with two washes of the peptide resin with 20% piperidine in DMF (5 minutes wash followed by 20 minutes wash).

The N-terminal Glac residue was introduced manually in two steps. In the first step, bromoacetic acid or chloroacetic acid was coupled on the resin using diisopropylcarbodiimide (DIC) as a coupling reagent. In the second step, the resin was reacted with D-glucamine (4 equivalents) in NMP to displace the halogen. The N-bromoacetyl peptide resins were reacted with D-glucamine at room temperature and the N-chloroacetyl peptide resins were reacted at 50° C. D-Glucamine has limited solubility in NMP. The reactions can be executed with D-glucamine suspended in NMP. Optionally, D-glucamine was first reacted with N,O-bis(trimethylsilyl)acetamide (BSA, 3-6 equivalents) in NMP for up to 1 hour to give a solution of silylated D-glucamine. Then the solution was added to the N-haloacetyl peptide resin. The reactions with D-glucamine were run for approximately 16 hours.

Upon completion of the peptide synthesis, the peptide resins were washed with DCM. The resins were treated with 95% TFA/water and TIS (up to 5% v/v) for 2 hours to remove the side-chain protecting groups with concomitant cleavage of the peptide from the resin. Most of the cleavage cocktail was evaporated, the crude peptides were precipitated with diethyl ether and separated by centrifugation or filtration.

The crude peptides were dissolved in up to 10 mL of water-acetonitrile mixtures and loaded onto a preparative HPLC column.

Each crude peptide was purified with a trifluoroacetic acid (TFA) buffer, which contained 0.01% TFA in water as Component A and 0.01% TFA in 95% acetonitrile as Component B. The peptides were eluted with a gradient of component B. The fractions with a purity exceeding 95%, determined by reverse-phase analytical HPLC, were pooled lyophilized. The compounds prepared were typically found to be at least 95% pure.

Syntheses of specifically illustrated compounds are provided below.

Example 1

Synthesis of Compound 1

The starting 2-chlorotrityl polystyrene resin (Peptides International, catalog number RCT-1083-PI, 1.39 mmol/g), 1.87 g, 2.6 mmol) was reacted with a solution of Fmoc-D-1-Nal (1.3 mmol) and N,N-diisopropylethylamine (DIPEA, 6.5 mmol) in DCM (25 ml) for 2.5 hours. After MeOH (2.5 ml) was added, the mixture was rotated for another 30 minutes. The reagents were drained and the resin was washed with DMF. The resin was split between two 40 ml reaction vessels (0.65 mmol per vessel).

Solid phase peptide synthesis was performed using Tribute peptide synthesizer. Couplings of Fmoc-protected amino acids on the Tribute synthesizer were mediated with HBTU/NMM in DMF. Single cycles of 60 minutes with 2.5 mmol of activated Fmoc-protected amino acids per vessel (3.8-fold excess) were used during the synthesis. Arginine was coupled over 3 hours. Removal of the Fmoc protecting group was monitored by UV. Multiple (up to 10 times, as needed) two-minute washes of the peptide resin with 20% piperidine in DMF were performed. The following amino acids were sequentially coupled: Fmoc-Pro-OH, Fmoc-His(Trt)-OH, Fmoc-Val-OH, Fmoc-Tyr(tBu)-OH, Fmoc-Val-OH, Fmoc-Arg(Pbf)-OH, Boc-Sar-OH. At the conclusion of the automated synthesis the resins from the two reaction vessels were combined.

The crude peptide was cleaved from the resin with 30 mL of 95% TFA/H$_2$O and 1 mL TIS for 2 hours. After the solvent was evaporated, the crude peptide was precipitated with diethyl ether, isolated by centrifugation, and was dried in-vacuo. Yield of the crude peptide: 1.513 g.

The crude peptide was dissolved in 20 mL of 50% acetonitrile. The peptide was purified by preparative HPLC on the 50×100 mM column in two runs, loading 10 ml of the crude peptide solution per run. The fractions of lesser purity were combined and were re-loaded on the HPLC column. The pure fractions from the three runs were pooled and lyophilized to give the target Compound 1 as a white powder. Yield: 521.1 mg (29% based on 74.3% peptide content).

The observed and calculated MS data (i.e., M+H) are provided in Table 3 below.

Example 2

Synthesis of Compound 4

The peptide was assembled manually starting from 13.158 g (20 mmol) of 2-chorotrityl polystyrene resin (Peptides International, catalog number RCT-1083-PI, 1.52 mmol/g). A solution of Fmoc-D-Phe(2-Cl) (4.219 g, 10 mmol) and DIPEA (8.8 ml, 50 mmmol) in DCM (75 ml) was added to the dry resin. The reaction was run for 6 hours. After methanol (8 ml) was added, the mixture was agitated for 30 minutes, the reagents were drained, and the resin was washed with DMF.

From this point on DIC/Oxyma Pure mediated couplings in NMP were employed. Single cycles of at least 2 hours and up to 24 hours with up to 2-fold excess of activated Fmoc-protected amino acids were used during the synthesis. The completeness of couplings was assessed with ninhydrin test. Removal of the Fmoc protecting group was achieved with two washes of the peptide resin with 20% piperidine in DMF (5 minutes wash followed by 20 minutes wash).

First, the (6-8) fragment was assembled by sequential coupling of Fmoc-Pro-OH and Fmoc-His(Trt)-OH, followed by removal of N-terminal Fmoc. The resin was washed with DCM and dried in-vacuo. The weight of the dried resin was 17.82 g; substitution was 0.56 mmol/g.

The synthesis was continued with 14.29 g (8 mmol) of the (6-8) resin. The following amino acid derivatives were coupled sequentially: Fmoc-Val-OH, Fmoc-Tyr(tBu)-OH, Fmoc-Val-OH, Fmoc-Arg(Pbf)-OH. The N-terminal Fmoc group was removed to give the (2-8) peptide resin.

At this point the resin was split into two unequal portions: the larger portion (5/8, 5 mmol) was used in the continuing synthesis of Compound 4 and the smaller portion (3/8, 3 mmol) was used in the synthesis of Compound 29 (see below). Boc-Sar-OH (10 mmol) was coupled on the larger portion of the resin to conclude solid-phase peptide synthesis of Compound 4.

The crude peptide was cleaved from the resin with 80 mL of 95% TFA/H$_2$O and 4 ml TIS for 2 hours. After the solvent was evaporated, the crude peptide was precipitated with diethyl ether, collected by filtration, and dried in-vacuo.

The precipitate (5.01 g) was dissolved in 50 mL of 50% acetonitrile. The peptide was purified by preparative HPLC on the 50×100 mM column in five runs, loading 10 ml of the crude peptide solution per run. The pure fractions were pooled and lyophilized to give the target Compound 4 as a white powder. Yield: 3039 mg (45% based on 75% peptide content).

The observed and calculated MS data (i.e., M+H) are provided in Table 3 below.

Example 3

Synthesis of Compound 9

The peptide was assembled manually starting from 58.8 g (100 mmol) of 2-chlorotrityl polystyrene resin (CreoSalus CAT #SC5055, substitution 1.7 mmol/g;). A solution of Fmoc-D-Phe(2-Me)-OH (28.1 g, 70 mmol) and DIPEA (49.3 ml, 280 mmmol) in DCM (450 ml) was added to the dry resin. The reaction was run for 2 hours. After methanol (75 ml) was added, the mixture was agitated for 10 minutes and the reagents were drained. The resin was washed with 3× DCM/MeOH/DIEA (17:2:1, v/v/v), 2× DCM, 2× DMF, and 2× DCM.

From this point on DIC/Oxyma Pure mediated couplings in NMP were employed. Single cycles of at least 2 hours and up to 16 hours with up to 2-fold excess of activated Fmoc-protected amino acids were used during the synthesis. The completeness of couplings was assessed with ninhydrin test. Removal of the Fmoc protecting group was achieved with two washes of the peptide resin with 20% piperidine in DMF (10 minutes wash followed by 30 minutes wash).

First, the (2-8) fragment was assembled by sequential coupling of Fmoc-Pro-OH, Fmoc-His(Trt)-OH, Fmoc-Val-OH, Fmoc-Tyr(tBu)-OH, Fmoc-Val-OH, Fmoc-Arg(Pbf)-OH. The N-terminal Fmoc group on arginine was removed.

At this point the resin was split into two unequal portions. The larger portion (3/5, 42 mmol) was used in the continuing synthesis of Compound 9.

Boc-Sar-OH (65 mmol) was coupled on the larger portion of the resin to conclude solid-phase peptide synthesis of Compound 9.

98.6 g of the peptide resin was added to 1 L of cold cocktail TFA/TES/$H_2O$ (94:3:3, v/v/v). The mixture was agitated at room temperature for 3 h. The mixture was filtered and resin beads were washed with 95% TFA (3×70 mL). The filtrate was rotary evaporated to reduce the volume to approximately 150 mL. Diethyl ether (500 mL) was added. The precipitate was collected by filtration, washed with ether, and then dried to give the crude product (43.9 g).

HPLC purification of the crude peptide was performed on a C18 column (101.6×250 mm, 16 μm particle size, 100 Å pore size, Kromasil). Component A was 0.1% TFA and component B was 0.1% TFA in 60% acetonitrile. The combined fractions, containing target compound 9 as a TFA salt, were reloaded on the column for salt exchange. The column was washed with 4 L of 3% acetonitrile in 0.1 M ammonium acetate solution, pH 4.5. Acetate buffer system was used to elute the compound. Component A of the acetate buffer system was 1% AcOH and component B was 1% AcOH in 60% acetonitrile. The combined fractions were lyophilized to give target Compound 9 as an acetate salt. Yield: 29.532 g (57.9% based on 82.5% peptide content).

The observed and calculated MS data (i.e., M+H) are provided in Table 3 below.

Example 4

Synthesis of Compound 29

The (2-8) peptide resin described in Example 2 above (3 mmol) was thoroughly washed with NMP. A solution of chloroacetic acid (15 mmol) and DIC (15 mmol) in NMP (50 mL) was added and the coupling was run for 5 hours. The reagents were drained and the resin was washed with NMP. The resin was transferred into a reaction vessel compatible with microwave peptide synthesizer Liberty Blue and was washed with NMP one more time. Solid D-glucamine (12 mmol) was added on top of the wet resin and the vessel was placed inside the reaction chamber of Liberty Blue. NMP (30 ml) was delivered and the reaction mixture was heated at 50° C. by microwave irradiation with concomitant nitrogen agitation for 16 hours. The resin was then sequentially washed with DMF, water, methanol and DCM.

The crude peptide was cleaved from the resin with 60 mL of 95% TFA/$H_2O$ and 3 ml TIS for 2 hours. After the solvent was evaporated, the crude peptide was precipitated with diethyl ether and isolated by centrifugation.

The precipitate was dissolved in 40 mL of 50% acetonitrile. The peptide was purified by preparative HPLC on the 50×100 mM column in four runs, loading 10 ml of the crude peptide solution per run. The pure fractions were pooled and lyophilized to give the target Compound 29 as a white powder. Yield: 2013.5 mg (46% based on 80% peptide content).

The observed and calculated MS data (i.e., M+H) are provided in Table 3 below.

Example 5

Synthesis of Compound 43

The starting 2-chlorotrityl polystyrene resin (Peptides International, (catalog number RCT-1083-PI, 1.5 mmol/g, 949 mg, 1.5 mmol) was reacted with a solution of Fmoc-D-Phe(2-Cl) (316 mg, 0.75 mmol, Chem-Impex) and DIPEA (3.75 mmol, 660 ul) in DCM (10 ml) for 4 hours. After MeOH (1 ml) was added, the mixture was rotated for another 30 minutes. The reagents were drained and the resin was washed with DMF. One-third of this resin (0.25 mmol) was placed in a Symphony reaction vessel and was used in the synthesis of Compound 46 using the Symphony peptide synthesizer.

Couplings of Fmoc-protected amino acids on the Symphony synthesizer were mediated with HBTU/DIPEA in NMP. Single cycles of 60 minutes with a 4-fold excess of activated Fmoc-protected amino acids were used during the synthesis. Arginine was coupled over 3 hours. Removal of the Fmoc protecting group was accomplished with two washes of the peptide resin with 20% piperidine in DMF (5 minutes wash followed by 20 minutes wash). The following amino acids were sequentially coupled: Fmoc-Pro-OH, Fmoc-His(Trt)-OH, Fmoc-Cyclopentylglycine-OH, Fmoc-Tyr(tBu)-OH, Fmoc-Val-OH, and Fmoc-Arg(Pbf)-OH. The N-terminal Fmoc group was removed and the resin was washed with NMP.

A solution of bromoacetic acid (2.5 mmol) and DIC (2.5 mmol) in NMP (5 ml) was added to the resin. The reaction was run for 4 h. The reagents were drained and the resin was washed with NMP. D-Glucamine (1 mmol) was suspended in NMP (5 ml). N,O-Bis(trimethylsilyl)acetamide (3 mmol) was added to the suspension. The mixture was stirred for 30 minutes, during which time most of D-glucamine dissolved. The near-clear solution of silylated D-glucamine was added to the resin. The reaction was run overnight. The regents were drained and the resin was washed with NMP, MeOH and DCM.

The crude peptide was cleaved from the resin with 5 mL of 95% TFA/$H_2O$ and 0.2 mL TIS for 2 hours. After the solvent was evaporated, the crude peptide was precipitated with diethyl ether and isolated by centrifugation.

The precipitate was dissolved in 5 mL of 50% acetonitrile. The peptide was purified by preparative HPLC on the 30×100 mM column. The pure fractions were pooled and lyophilized to give the target compound 43 as a white powder. Yield: 66.6 mg (17% based on 78.7% peptide content).

The observed and calculated MS data (i.e., M+H) are provided in Table 3 below.

Example 6

Synthesis of Compound 46

The starting 2-chlorotrityl polystyrene resin (Peptides International, (catalog number RCT-1083-PI, 1.52 mmol/g), 2.632 g, 4 mmol) was reacted with a solution of Fmoc-D-Phe(2-Me) (2 mmol) and DIPEA (10 mmol) in DCM (20 ml) for 4 hours. After MeOH (2 ml) was added, the mixture was rotated for another 30 minutes. The reagents were drained and the resin was washed with DMF. Half of the resin (1 mmol) was split between four Symphony reaction vessels (0.25 mmol per vessel). Solid phase peptide synthesis was continued on Symphony peptide synthesizer in parallel, using an identical coupling protocol for each vessel.

Couplings of Fmoc-protected amino acids on the Symphony synthesizer were mediated with HBTU/DIPEA in NMP. Single cycles of 60 minutes with a 4-fold excess of activated Fmoc-protected amino acids were used during the synthesis. Arginine was coupled over 3 hours. Removal of the Fmoc protecting group was accomplished with two washes of the peptide resin with 20% piperidine in DMF (5 minutes wash followed by 20 minutes wash). The following amino acids were sequentially coupled: Fmoc-Pro-OH, Fmoc-His(Trt)-OH, Fmoc-Cyclohexylglycine-OH, Fmoc-Tyr(tBu)-OH, Fmoc-Val-OH, and Fmoc-Arg(Pbf)-OH. The N-terminal Fmoc group was removed and the resins were combined within a 40 ml quartz reaction vessel compatible with the Tribute peptide synthesizer. The (2-8) peptide resin was thoroughly washed with NMP.

A solution of chloroacetic acid (5 mmol) and DIC (5 mmol) in NMP (15 mL) was added and the coupling was run for 16 hours on the Tribute synthesizer. The reagents were drained and the resin was washed with NMP. Solid D-glucamine (4 mmol) was added on top of the wet resin followed by NMP (20 ml). The reaction vessel was placed on the Tribute synthesizer and was heated at 50° C. by IR irradiation with concomitant vortexing for 16 hours. The resin was then sequentially washed with DMF, water, methanol and DCM.

The crude peptide was cleaved from the resin with 20 mL of 95% TFA/H$_2$O and 0.5 ml TIS for 2 hours. After the solvent was evaporated, the crude peptide was precipitated with diethyl ether and isolated by centrifugation.

The precipitate was dissolved in 20 mL of 50% acetonitrile. The peptide was purified by preparative HPLC on the 50×100 mM column in two runs, loading 10 ml of the crude peptide solution per run. The pure fractions were pooled and lyophilized to give the target compound 46 as a white powder. Yield: 601.2 mg (38% based on 75.7% peptide content).

The observed and calculated MS data (i.e., M+H) are provided in Table 3 below.

Example 7

Synthesis of Compound 31

The starting 2-chlorotrityl polystyrene resin (Peptides International, (catalog number RCT-1083-PI, 1.58 mmol/g), 1.266 g, 2 mmol) was reacted with a solution of Fmoc-D-Phe(2-Cl) (422 mg, 1 mmol) and DIPEA (880 μl, 5 mmol) in DCM (10 ml) for 4 hours. MeOH (1 ml) was added and the mixture was rotated for another 30 minutes. The reagents were drained and the resin was washed with DMF. The resin was split between four Symphony reaction vessels (0.25 mmol per vessel). Solid phase peptide synthesis was continued on Symphony peptide synthesizer in parallel, using an identical coupling protocol for each vessel.

Couplings of Fmoc-protected amino acids on the Symphony synthesizer were mediated with HBTU/DIPEA in NMP. Single cycles of 60 minutes with a 4-fold excess of activated Fmoc-protected amino acids were used during the synthesis. Arginine was coupled over 3 hours. Removal of the Fmoc protecting group was accomplished with two washes of the peptide resin with 20% piperidine in DMF (5 minutes wash followed by 20 minutes wash). The following amino acids were sequentially coupled: Fmoc-Pro-OH, Fmoc-His(Trt)-OH, Fmoc-Cyclohexylglycine-OH, Fmoc-Tyr(tBu)-OH, Fmoc-Val-OH, and Fmoc-Arg(Pbf)-OH. The N-terminal Fmoc group was removed and the resins were combined within a manual peptide synthesis vessel. The (2-8) peptide resin was thoroughly washed with NMP.

A solution of bromoacetic acid (1.389 g, 10 mmol) and DIC (1.54 ml, 10 mmol) in NMP (20 mL) was added and the coupling was run overnight. The reagents were drained and the resin was washed with NMP.

D-glucamine (725 mg, 4 mmol) was suspended in NMP (40 ml), followed by addition of N,O-bis(trimethylsilyl) acetamide. The mixture was stirred for 30 min. to give a near-clear solution of silylated D-glucamine. The solution was added to the resin and the reaction was run overnight. The resin was then sequentially washed with DMF, methanol and DCM.

The crude peptide was cleaved from the resin with 20 mL of 95% TFA/H$_2$O and 0.5 ml TIS for 2 hours. After the solvent was evaporated, the crude peptide was precipitated with diethyl ether and isolated by centrifugation.

The precipitate was dissolved in 20 mL of 50% acetonitrile. The peptide was purified by preparative HPLC on the 50×100 mM column in two runs, loading 10 ml of the crude peptide solution per run. The pure fractions were pooled and lyophilized to give the target Compound 31 as a white powder. Yield: 384 mg (32% based on 83.5% peptide content).

The observed and calculated MS data (i.e., M+H) are provided in Table 3 below.

Example 8

Synthesis of Compounds 2, 3, 5-8, 10-28, 30, 32-42, 44 and 45

Compounds 2, 3, 5-8, 10-28, 30, 32-42, 44, and 45 were synthesized by using the methods described in Examples 1-7.

The observed and calculated MS data (i.e., M+H) of Compounds 1-46, as well as the purity of these compounds, are summarized in Table 3 below.

TABLE 3

| Compound No. | Calculated M + H | Observed M + H | % Purity |
|---|---|---|---|
| 1 | 1038.5 | 1038.8 | 96.7 |
| 2 | 1067.6 | 1067.7 | 100.0 |
| 3 | 1056.5 | 1056.6 | 99.5 |
| 4 | 1022.5 | 1022.7 | 98.2 |
| 5 | 1013.5 | 1013.7 | 100.0 |
| 6 | 1064.6 | 1064.7 | 97.9 |
| 7 | 1056.5 | 1056.5 | 99.5 |
| 8 | 1016.6 | 1016.7 | 98.7 |
| 9 | 1002.5 | 1002.6 | 98.4 |
| 10 | 1044.6 | 1044.4 | 98.7 |
| 11 | 1066.4 | 1066.6 | 99.0 |
| 12 | 1102.5 | 1102.6 | 98.9 |
| 13 | 1101.6 | 1101.7 | 97.0 |
| 14 | 1092.6 | 1092.7 | 98.9 |
| 15 | 1064.6 | 1064.7 | 99.4 |
| 16 | 1086.5 | 1086.7 | 100.0 |
| 17 | 1054.5 | 1054.7 | 99.6 |
| 18 | 1048.5 | 1048.7 | 86.5 |
| 19 | 1062.5 | 1062.7 | 100.0 |
| 20 | 1085.5 | 1085.6 | 98.2 |
| 21 | 1038.5 | 1038.7 | 99.1 |
| 22 | 1076.5 | 1076.5 | 96.6 |
| 23 | 1076.5 | 1076.5 | 97.5 |
| 24 | 1077.4 | 1077.5 | 94.9 |
| 25 | 1036.5 | 1036.5 | 98.5 |
| 26 | 1096.6 | 1096.7 | 99.8 |
| 27 | 1042.6 | 1042.7 | 98.7 |
| 28 | 1056.5 | 1056.6 | 95.2 |
| 29 | 1172.5 | 1172.6 | 100.0 |
| 30 | 1022.5 | 1022.5 | 86.5 |
| 31 | 1212.6 | 1212.7 | 99.7 |
| 32 | 1038.5 | 1038.5 | 98.3 |
| 33 | 1021.5 | 1021.5 | 98.5 |
| 34 | 1078.6 | 1078.7 | 95.6 |
| 35 | 1084.5 | 1084.6 | 99.2 |
| 36 | 1104.6 | 1104.7 | 97.4 |
| 37 | 1188.6 | 1188.7 | 97.1 |
| 38 | 1194.6 | 1194.7 | 99.7 |
| 39 | 1214.6 | 1214.7 | 99.3 |
| 40 | 1228.6 | 1228.7 | 96.2 |
| 41 | 1234.6 | 1234.7 | 97.7 |
| 42 | 1254.6 | 1254.7 | 100.0 |
| 43 | 1198.6 | 1198.6 | 99.5 |
| 44 | 1178.6 | 1178.8 | 97.2 |
| 45 | 1152.6 | 1152.8 | 99.5 |
| 46 | 1192.6 | 1192.9 | 99.1 |

Example 9

AT1 Receptor Agonist and Antagonist Activity Measured by FLIPR Assay

AT1 receptor (AT1R) agonists increase intracellular flux of calcium ions. AT1R antagonists can reduce the agonist effect. Agonist and antagonist activity of Compounds 1-46 described above was assessed in a cell-based Fluorescence Imaging Plate Reader (FLIPR) assay. Compounds were first tested for agonism (Part I) followed by addition of the AT1R agonist angiotensin II to test for antagonist activity (Part II). This assay used a stable hAT1R expressing cell line (ChanTest hAT1R; ChanTest Corp A628). Intracellular flux of calcium in response to agonist was measured through real-time measurement of fluorescence induced through the interaction of Ca2+ (released from intracellular stores) and calcium-sensitive dye. In Part I, cells were exposed to varying concentrations of test compounds and immediately measured for agonist activity (EC50 and Efficacy). In Part II, following a 20-minute incubation with test compounds, a fixed concentration of agonist (Angiotensin II) was added and the resulting fluorescence again was measured to determine antagonist activity (IC50 and Efficacy).

ChanTest hAT1R stable cells were maintained in Ham's F12 containing 10% (v/v) heat inactivated fetal bovine serum (FBS-HI), 4 mM Glutamax, 1% NEAA, 50 ng/mL plasmocin, 400 µg/mL G418 at 37° C. under 5% $CO_2$ in a humidified atmosphere.

For FLIPR assay, ChanTest hAT1R cells were trypsinized with 6 ml of Trypsin EDTA solution and harvested in phenol-red free DMEM containing 10% FBS-HI, 4 mM Glutamax and counted, spun down and resuspended in the same medium. The cell suspension was added to the wells of 384-well black PDL clear bottom plates at $2.5 \times 10^4$ cells/well, 20 µl/well.

FLIPR Assay

Preparation of Loading Buffer:
  Loading Buffer: 1 vial of Calcium 5 Bulk Assay reagent was dissolved in 100 ml of 1× HBSS-20 mM Hepes buffer.
  Probenecid was resuspended at 1 M in 1 M NaOH. Once the probenecid had gone into solution, an equal volume of $H_2O$ was added to make a solution of 500 mM followed by a 1:100 dilution in the Loading Buffer for a working concentration of 5 mM. The pH was adjusted to 7.4 using 1 M NaOH.

Loading the Cells with Loading Buffer
  Cell plates were removed from the incubator and 25 µl of Loading Buffer containing probenecid (5 mM) added to each well.
  Plates were incubated for 1 hour at 37° C. under 5% CO2 in a humidified atmosphere.

Acquisition of Calcium Image
  FLIPR Tetra was setup with the following default parameters and a read mode with an excitation wavelength of 470-495 nm and an emission wavelength of 515-575 nm as determined by filter selection:
  Gain of 50
  Excitation Intensity of 80% (Default)
  Exposure Time of 0.4 seconds (Default)
  The cell plate was transferred to the FLIPR Tetra, along with the 384 well compound plate. The remaining steps of the assay were carried forward by FLIPR Tetra. A baseline reading was taken at 1-second (s) intervals for 10 s followed by the addition of 5 µl of 10× compounds. The compound-induced fluorescence signal was then measured for 3 minutes with readings taken at 1-s intervals.
  The cell plate was removed from the FLIPR and set aside for an additional 17 minutes.
  The cell plate was then transferred back to the FLIPR Tetra, along with the 384 well Angiotensin II agonist dilution plate. A baseline reading was taken at 1-second (s) intervals for 10 seconds, followed by the addition of 5.5 µl of 10× Angiotensin II agonist. The agonist-induced fluorescence signal was then measured for 3 minutes with readings taken at 1-s intervals.
  Overall, each well in the FLIPR assay was composed of the following components in a total volume of 55.5 µl:

| 20 µl | $2.5 \times 10^4$ cells |
| 25 µl | Calcium 5 Loading Buffer |
| 5 µl | 10× test or reference compound |
| 5.5 µl | 10× Angiotensin II agonist (10 nM final concentration) |

Time-course results from the FLIPR Calcium 5 assay were expressed as relative fluorescence light units (RFU). The maximum minus minimum values (Max−Min) were used to quantify the strength of the signal. Mean RFU were calculated from replicate values and plotted on the y-axis versus compound concentration on a logarithmic scale on the x-axis, and a single-binding site, four parameter concentration response model: (MIN+((MAX−MIN)/(1+((EC50/x)^Hill)))), was used to perform non-linear regression analysis, generating concentration response curves. Reported parameters included agonist potency EC50 (the concentration causing half-maximal agonist response), antagonist potency IC50 (the concentration causing half-maximal inhibition of the agonist response for antagonist compounds) and efficacy (% MPE: percent of the maximal possible effect).

Compounds 1-46 and four reference compounds were tested in the above assay. The four references compounds are: (1) sarilesin (i.e., [Sar1, Ile8]AngII: Sar-Arg-Val-Tyr-Ile-His-Pro-Ile-OH, ("Reference Compound 1"), (2) [Sar1, D-Phe8]AngII: Sar-Arg-Val-Tyr-Ile-His-Pro-D-Phe-OH ("Reference Compound 2"), Samanen et al. *J. Med.Chem* 1988, 31, 510-516, (3) Angiotensin II: Asp-Arg-Val-Tyr-Ile-His-Pro-Phe-OH (i.e., an endogenous agonist having no antagonist activity) ("Reference Compound 3"), and (4) valsartan ("Reference Compound 4"). The results are summarized in Table 4 below.

As shown in Table 4, Compounds 1-46 exhibited similar antagonistic activity as reference antagonists (i.e. Reference Compounds 1, 2 and 4) and had significantly reduced agonist activities compared to reference peptidic AT1R antagonists (i.e., Reference Compounds 1 and 2), which suggests that these compounds can be used to treat disorders (e.g., hypertension disorders, preeclampsia, or renal diseases) in patients during pregnancy without causing an unwanted pressor effect.

TABLE 4

| Cpd No. | hAT1R Agonist Efficacy Agonist (%) Ave | hAT1R Antagonist IC50 Ave (nM) | hAT1R Antagonist Efficacy Antag (%) Ave |
|---|---|---|---|
| 1 | 5 | 10.6 | 99 |
| 2 | 1 | 16.5 | 100 |
| 3 | 5 | 23.6 | 99 |
| 4 | 6 | 10.7 | 99 |
| 5 | 5 | 59.6 | 100 |
| 6 | 10 | 16.6 | 99 |
| 7 | 12 | 6.4 | 99 |
| 8 | 3 | 8.5 | 101 |
| 9 | 4 | 13.9 | 99 |
| 10 | 5 | 9.5 | 99 |
| 11 | 4 | 8.7 | 99 |
| 12 | 5 | 3.4 | 100 |
| 13 | 7 | 3.2 | 100 |
| 14 | 5 | 8.0 | 100 |
| 15 | 6 | 4.6 | 100 |
| 16 | 6 | 5.0 | 99 |
| 17 | 4 | 6.0 | 100 |
| 18 | 3 | 10.1 | 99 |
| 19 | 8 | 14.1 | 99 |
| 20 | 5 | 5.2 | 99 |
| 21 | 2 | 10.6 | 99 |
| 22 | 3 | 5.0 | 99 |
| 23 | 4 | 5.2 | 98 |
| 24 | 4 | 7.0 | 99 |
| 25 | 2 | 11.6 | 100 |
| 26 | 12 | 32.9 | 99 |
| 27 | 8 | 14.5 | 100 |
| 28 | 5 | 12.2 | 99 |
| 29 | 6 | 19.5 | 99 |
| 30 | 12 | 20.5 | 100 |
| 31 | 6 | 15.7 | 99 |
| 32 | 5 | 24.1 | 99 |
| 33 | 3 | 17.1 | 100 |
| 34 | 5 | 15.5 | 100 |
| 35 | 6 | 14.3 | 100 |
| 36 | 13 | 26.0 | 100 |
| 37 | 7 | 19.5 | 99 |
| 38 | 5 | 18.8 | 101 |
| 39 | 8 | 26.7 | 101 |
| 40 | 5 | 21.9 | 101 |
| 41 | 5 | 19.1 | 101 |
| 42 | 10 | 28.5 | 101 |
| 43 | 6 | 16.6 | 100 |
| 44 | 7 | 20.4 | 101 |
| 45 | 6 | 18.6 | 101 |
| 46 | 6 | 22.2 | 100 |
| Ref. Cpd. 1 | 42 | 14.2 | 99 |
| Ref. Cpd. 2 | 25 | 14.3 | 99 |
| Ref. Cpd. 3 | 100 | N/A | N/A |
| Ref. Cpd. 4 | 0.7 | 40.7 | 100 |

Example 10

Evaluation in an In Vivo Animal Model of Preeclampsia

Compounds described in this disclosure were evaluated in an in vivo animal model of preeclampsia, as described by Hering, et al., Hypertension 2010, 56, 311-318 with modifications. Briefly, timed-pregnant vendor-catheterized (jugular and carotid vessels) rats arrived on gestational day (GD) 10, for use in experiments from GD13 to 20. Maternal body weights (BW) from GD10-12 were used to help predict pregnancy status for treatment designation. On GD12, rats were assigned to treatment groups. On GD13, rats were typically implanted with ALZET® pumps (osmotic infusion pumps for continuous dosing), one containing angiotensin II (or saline for control rats, IV infusion) and one containing a test compound (or vehicle for control rats, SC infusion). From GD14 to GD20, daily BW measurements were performed. Within GD14 to GD19, mean arterial pressure (MAP) measurements were taken at least on two separate days (GD14 and GD17), but may be as often as daily. On GD19, following final MAP measurement, rats were placed in metabolic cages for 4 hours for urine collection. Urine samples were centrifuged and the supernatant analyzed by rat albumin ELISA to test for albuminuria.

Compounds described in this disclosure showed reduction in MAP and albuminuria compared with vehicle on Day 19, indicating improvement of gestational hypertension and proteinuria associated with preeclampsia.

Other embodiments are within the scope of the following claims.

What is claimed is:

1. A compound of formula (I) or a pharmaceutically acceptable salt thereof:

AA1-Arg-Val-AA4-AA5-His-Pro-AA8-OH    (I), wherein
   AA1 is an amino acid residue selected from the group consisting of sarcosine and ((2S,3R,4R,5R)-2,3,4,5,6-pentahydroxyhexyl)glycine;
   AA4 is an amino acid residue selected from the group consisting of tyrosine or meta-tyrosine, each of which is optionally substituted with at least one substituent selected from the group consisting of halo and hydroxyl;

AA5 is an amino acid residue selected from the group consisting of valine, leucine, isoleucine, glycine, alanine, phenylalanine, threonine, lysine, and tyrosine, each of which is optionally substituted with at least one substituent selected from the group consisting of $C_{1-6}$ alkyl, $C_{4-6}$ cycloalkyl, $NH_2$, aryl, and heteroaryl; and AA8 is a D-amino acid residue selected from the group consisting of D-1-naphthylalanine, D-(3-benzothienyl)alanine, and D-phenylalanine substituted with at least one substituent selected from the group consisting of $C_{1-6}$ alkyl, $C_{1-6}$ haloalkyl, $C_{4-6}$ cycloalkyl, halo, CN, aryl, and heteroaryl, in which one said substituent is at the 2-position on the phenyl ring of the D-phenylalanine;

wherein each of Arg, Val, AA4, AA5, His, and Pro in formula (I) is an L-amino acid residue.

2. The compound of claim 1, wherein AA4 is tyrosine optionally substituted with at least one substituent, in which the at least one substituent is at the 3-position on the phenyl ring of the tyrosine.

3. The compound of claim 2, wherein AA4 is tyrosine, meta-tyrosine, 3-hydroxytyrosine, or 3-chlorotyrosine.

4. The compound of claim 1, wherein AA5 is an amino acid residue selected from the group consisting of valine, leucine, isoleucine, glycine, alanine, phenylalanine, threonine, lysine, and tyrosine, each of which is optionally substituted with at least one substituent selected from the group consisting of $CH_3$, cyclobutyl, cyclopentyl, cyclohexyl, $NH_2$, thienyl, and thiazolyl.

5. The compound of claim 4, wherein AA5 is valine, isoleucine, cyclobutylglycine, cyclopentylglycine, cyclohexylglycine, cyclohexylalanine, leucine, o-methyl threonine, lysine, phenylalanine, tyrosine, 4-aminophenylalanine, 3-thienylalanine, 2-thienylalanine, or 4-thiazolylalanine.

6. The compound of claim 5, wherein AA5 is valine, isoleucine, cyclopentylglycine, cyclohexylglycine, or O-methyl threonine.

7. The compound of claim 1, wherein AA8 is an amino acid residue selected from the group consisting of D-1-naphthylalanine, D-(3-benzothienyl)alanine, and D-phenylalanine substituted with at least one substituent selected from the group consisting of $CH_3$, $CF_3$, Cl, Br, CN, and phenyl, in which at least one said substituent is at the 2-position on the phenyl ring of the D-phenylalanine.

8. The compound of claim 1, wherein AA8 is D-1-naphthylalanine, D-(3-benzothienyl)alanine, D-2-chlorophenylalanine, D-2-bromophenylalanine, D-2-methylphenylalanine, D-2-trifluoromethylphenylalanine, D-2-cyanophenylalanine, D-2-phenylphenylalanine, D-2,4-dichlorophenylalanine, or D-2,6-dimethylphenylalanine.

9. The compound of claim 1, wherein AA1 is sarcosine.

10. The compound of claim 9, wherein AA4 is tyrosine, meta-tyrosine, 3-hydroxytyrosine, or 3-chlorotyrosine.

11. The compound of claim 10, wherein AA5 is valine, isoleucine, lysine, tyrosine, 4-aminophenylalanine, cyclohexylalanine, cyclopentylglycine, cyclohexylglycine, phenylalanine, O-methyl threonine, 3-thienylalanine, 2-thienylalanine, or 4-thiazolylalanine.

12. The compound of claim 11, wherein AA8 is D-1-naphthylalanine, D-(3-benzothienyl)alanine, D-2-chlorophenylalanine, D-2-bromophenylalanine, D-2-methylphenylalanine, D-2-trifluoromethylphenylalanine, D-2-cyanophenylalanine, D-2-phenylphenylalanine, D-2,4-dichlorophenylalanine, or D-2,6-dimethylphenylalanine.

13. The compound of claim 1, wherein AA1 is ((2S,3R,4R,5R)-2,3,4,5,6-pentahydroxyhexyl)glycine.

14. The compound of claim 13, wherein AA4 is tyrosine.

15. The compound of claim 14, wherein AA5 is valine or cyclohexylglycine.

16. The compound of claim 15, wherein AA8 is D-1-naphthylalanine, D-(3-benzothienyl)alanine, D-2-chlorophenylalanine, D-2-methylphenylalanine, or D-2-phenylphenylalanine.

17. The compound of claim 1, wherein the compound is
(1) Sar-Arg-Val-Tyr-Val-His-Pro-(D-1Nal)—OH;
(2) Sar-Arg-Val-Tyr-Lys-His-Pro-(D-1Nal)—OH;
(3) Sar-Arg-Val-Tyr-Val-His-Pro-(D-Phe(2-$CF_3$))—OH;
(4) Sar-Arg-Val-Tyr-Val-His-Pro-(D-Phe(2-Cl))—OH;
(5) Sar-Arg-Val-Tyr-Val-His-Pro-(D-Phe(2-CN))—OH;
(6) Sar-Arg-Val-Tyr-Val-His-Pro-(D-Phe(2-Ph))—OH;
(7) Sar-Arg-Val-Tyr-Val-His-Pro-(D-Phe(2,4-diCl))—OH;
(8) Sar-Arg-Val-Tyr-Val-His-Pro-(D-Phe(2,6-diMe))—OH;
(9) Sar-Arg-Val-Tyr-Val-His-Pro-(D-Phe(2-Me))—OH;
(10) Sar-Arg-Val-Tyr-Val-His-Pro-(D-(3-benzothienyl)alanine)—OH;
(11) Sar-Arg-Val-Tyr-Val-His-Pro-(D-Phe(2-Br))—OH;
(12) Sar-Arg-Val-Tyr-Tyr-His-Pro-(D-1Nal)—OH;
(13) Sar-Arg-Val-Tyr-Aph-His-Pro-(D-1Nal)—OH;
(14) Sar-Arg-Val-Tyr-Cha-His-Pro-(D-1Nal)—OH;
(15) Sar-Arg-Val-Tyr-Cpg-His-Pro-(D-1Nal)—OH;
(16) Sar-Arg-Val-Tyr-Phe-His-Pro-(D-1Nal)—OH;
(17) Sar-Arg-Val-Tyr-Thr(Me)-His-Pro-(D-1Nal)—OH;
(18) Sar-Arg-Val-Tyr-Cpg-His-Pro-(D-Phe(2-Cl))—OH;
(19) Sar-Arg-Val-Tyr-Chg-His-Pro-(D-Phe(2-Cl))—OH;
(20) Sar-Arg-Val-Tyr-Aph-His-Pro-(D-Phe(2-Cl))—OH;
(21) Sar-Arg-Val-Tyr-Thr(Me)-His-Pro-(D-Phe(2-Cl))—OH;
(22) Sar-Arg-Val-Tyr-(3-Thi)-His-Pro-(D-Phe(2-Cl))—OH;
(23) Sar-Arg-Val-Tyr-(2-Thi)-His-Pro-(D-Phe(2-Cl))—OH;
(24) Sar-Arg-Val-Tyr-(Ala(4-Thz))-His-Pro-(D-Phe(2-Cl))—OH;
(25) Sar-Arg-Val-Tyr-Ile-His-Pro-(D-Phe(2-Cl))—OH;
(26) Sar-Arg-Val-Tyr-Chg-His-Pro-(D-Phe(2-$CF_3$))—OH;
(27) Sar-Arg-Val-Tyr-Chg-His-Pro-(D-Phe(2-Me))—OH;
(28) Sar-Arg-Val-Tyr(3-Cl)-Val-His-Pro-(D-Phe(2-Cl))—OH;
(29) Glac-Arg-Val-Tyr-Val-His-Pro-(D-Phe(2-Cl))—OH;
(30) Sar-Arg-Val-(m-Tyr)-Val-His-Pro-(D-Phe(2-Cl))—OH;
(31) Glac-Arg-Val-Tyr-Chg-His-Pro-(D-Phe(2-Cl))—OH;
(32) Sar-Arg-Val-DOPA-Val-His-Pro-(D-Phe(2-Cl))—OH;
(33) Sar-Arg-Val-Aph-Val-His-Pro-(D-Phe(2-Cl))—OH;
(34) Sar-Arg-Val-Tyr-Chg-His-Pro-(D-1Nal)—OH;
(35) Sar-Arg-Val-Tyr-Chg-His-Pro-(D-(3-benzothienyl)alanine)—OH;
(36) Sar-Arg-Val-Tyr-Chg-His-Pro-(D-Phe(2-Ph))—OH;
(37) Glac-Arg-Val-Tyr-Val-His-Pro-(D-1Nal)—OH;
(38) Glac-Arg-Val-Tyr-Val-His-Pro-(D-(3-benzothienyl)alanine)—OH;
(39) Glac-Arg-Val-Tyr-Val-His-Pro-(D-Phe(2-Ph))—OH;
(40) Glac-Arg-Val-Tyr-Chg-His-Pro-(D-1Nal)—OH;
(41) Glac-Arg-Val-Tyr-Chg-His-Pro-(D-(3-benzothienyl)alanine)—OH;
(42) Glac-Arg-Val-Tyr-Chg-His-Pro-(D-Phe(2-Ph))—OH;

(43) Glac-Arg-Val-Tyr-Cpg-His-Pro-(D-Phe(2-Cl))—OH;
(44) Glac-Arg-Val-Tyr-Cpg-His-Pro-(D-Phe(2-Me))—OH;
(45) Glac-Arg-Val-Tyr-Val-His-Pro-(D-Phe(2-Me))—OH; or
(46) Glac-Arg-Val-Tyr-Chg-His-Pro-(D-Phe(2-Me))—OH.

18. The compound of claim 1, wherein the compound is:
(4) Sar-Arg-Val-Tyr-Val-His-Pro-(D-Phe(2-Cl))—OH;
(9) Sar-Arg-Val-Tyr-Val-His-Pro-(D-Phe(2-Me))—OH;
(29) Glac-Arg-Val-Tyr-Val-His-Pro-(D-Phe(2-Cl))—OH;
(31) Glac-Arg-Val-Tyr-Chg-His-Pro-(D-Phe(2-Cl))—OH;
(45) Glac-Arg-Val-Tyr-Val-His-Pro-(D-Phe(2-Me))—OH; or
(46) Glac-Arg-Val-Tyr-Chg-His-Pro-(D-Phe(2-Me))—OH.

19. The compound of claim 1, wherein AA8 is D-phenylalanine substituted at one or two positions with a substituent selected from the group consisting of $C_{1-6}$ alkyl, $C_{1-6}$ haloalkyl, $C_{4-6}$ clycloalkyl, halo, CN, aryl, an heteroaryl, wherein one said substituent is at the 2-position on the phenyl ring of the D-phenylalanine.

20. The compound of claim 1, wherein the compound exhibits angiotensin-1-receptor (AT1R) antagonist activity.

21. The compound of claim 1, wherein the compound exhibits reduces AT1R agonist activity as compared to sarilesin.

22. The compound of claim 18, wherein the compound is: Sar-Arg-Val-Tyr-Val-His-Pro-(D-Phe(2-Cl))—OH.

23. The compound of claim 18, wherein the compound is: Sar-Arg-Val-Tyr-Val-His-Pro-(D-Phe(2-Me))—OH.

24. The compound of claim 18, wherein the compound is: Glac-Arg-Val-Tyr-Val-His-Pro-(D-Phe(2-Me))—OH.

25. A pharmaceutical composition, comprising the compound of claim 1 and a pharmaceutically acceptable carrier.

26. A method of treating hypertension, comprising administering to a patient in need thereof an effective amount of the pharmaceutical composition of claim 25.

27. The method of claim 26, wherein the hypertension is induced by pregnancy.

28. A method of treating preeclampsia or a renal disease induced by pregnancy, comprising administering to a patient in need thereof an effective amount of the pharmaceutical composition of claim 25.

* * * * *